US006479244B1

(12) United States Patent
Belouchi et al.

(10) Patent No.: US 6,479,244 B1
(45) Date of Patent: Nov. 12, 2002

(54) METHOD FOR GENOTYPING MICROSATELLITE DNA MARKERS

(75) Inventors: Abdelmajid Belouchi, Montreal (CA); Bruno Paquin, Chateauguay (CA)

(73) Assignee: Galileo Genomics, St. Laurent (CA)

( * ) Notice: Subject to any disclaimer, the term of this patent is extended or adjusted under 35 U.S.C. 154(b) by 0 days.

(21) Appl. No.: 09/840,717

(22) Filed: Apr. 23, 2001

(51) Int. Cl.[7] ............... C12Q 1/68; C12P 19/34; C07H 21/04
(52) U.S. Cl. ............ 435/6; 435/91.1; 435/91.2; 536/23.1; 536/24.3; 536/24.33
(58) Field of Search ............ 435/6, 91.1, 91.2; 536/23.1, 24.33; 532/23.5

(56) References Cited

U.S. PATENT DOCUMENTS 6,303,301 B1 * 10/2001 Mack .................. 435/6

OTHER PUBLICATIONS

Zarytova et al. (Nucleosides and Nucleotides (1998) 17(9–11): 2143–2147).*

Zirvi et al. (Nuc. Acid Res. (1999) 27(24): e41).*

* cited by examiner

Primary Examiner—Kenneth R. Horlick
Assistant Examiner—Alexander H. Spiegler
(74) Attorney, Agent, or Firm—Gibbons, Del Deo, Dolan, Griffinger & Vecchione

(57) ABSTRACT

The present invention provides a high throughput method for genotyping microsatellite markers. The technology uses a combination of oligonucleotides in a selective ligation reaction that discriminates mono-, di-, tri-, tetra-, penta-, hexa-, hepta-, octa- and nona-nucleotide repeated alleles in amplified DNA from individuals.

26 Claims, 7 Drawing Sheets

OLIGONUCLEOTIDE LIGATION ASSAY OLAs

FIG. 2

OLIGONUCLEOTIDE LIGATION ASSAY PRINCIPLE

- DNA TEMPLATE IS A PCR-AMPLIFIED FRAGMENT CONTAINING THE REPEATED REGION
- CENTRAL PRIMER (PC) SEQUENCE EQUAL THE SHORTEST REPEAT REPORTED FOR A GIVEN ALLELE
- 5'-PRIMER (P5) IS OF UNIQUE LENGTH AND COMPLEMENTARY TO THE 3'-REPEAT-FLANKING SEQUENCE OF A GIVEN MARKER
- 3'-PRIMERS (P3s) ARE CONSTITUTED OF A CORE SEQUENCE COMPLEMENTARY TO THE 5'-REPEAT-FLANKING SEQUENCE OF A GIVEN MARKER AND EACH POSSESSES AT ITS 5'-END A NUMBER (n) OF REPEAT UNITS [X]n, WHICH IS DICTATED BY THE NUMBER OF ALLELES REPORTED AT THIS MARKER
- LIGATION (L) OF ADJACENT ONS

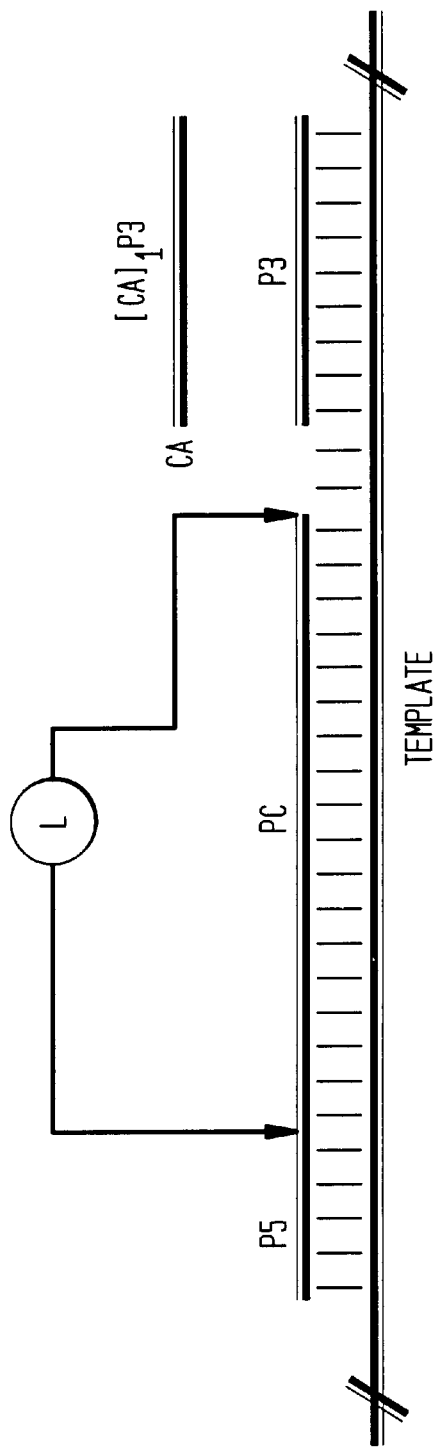

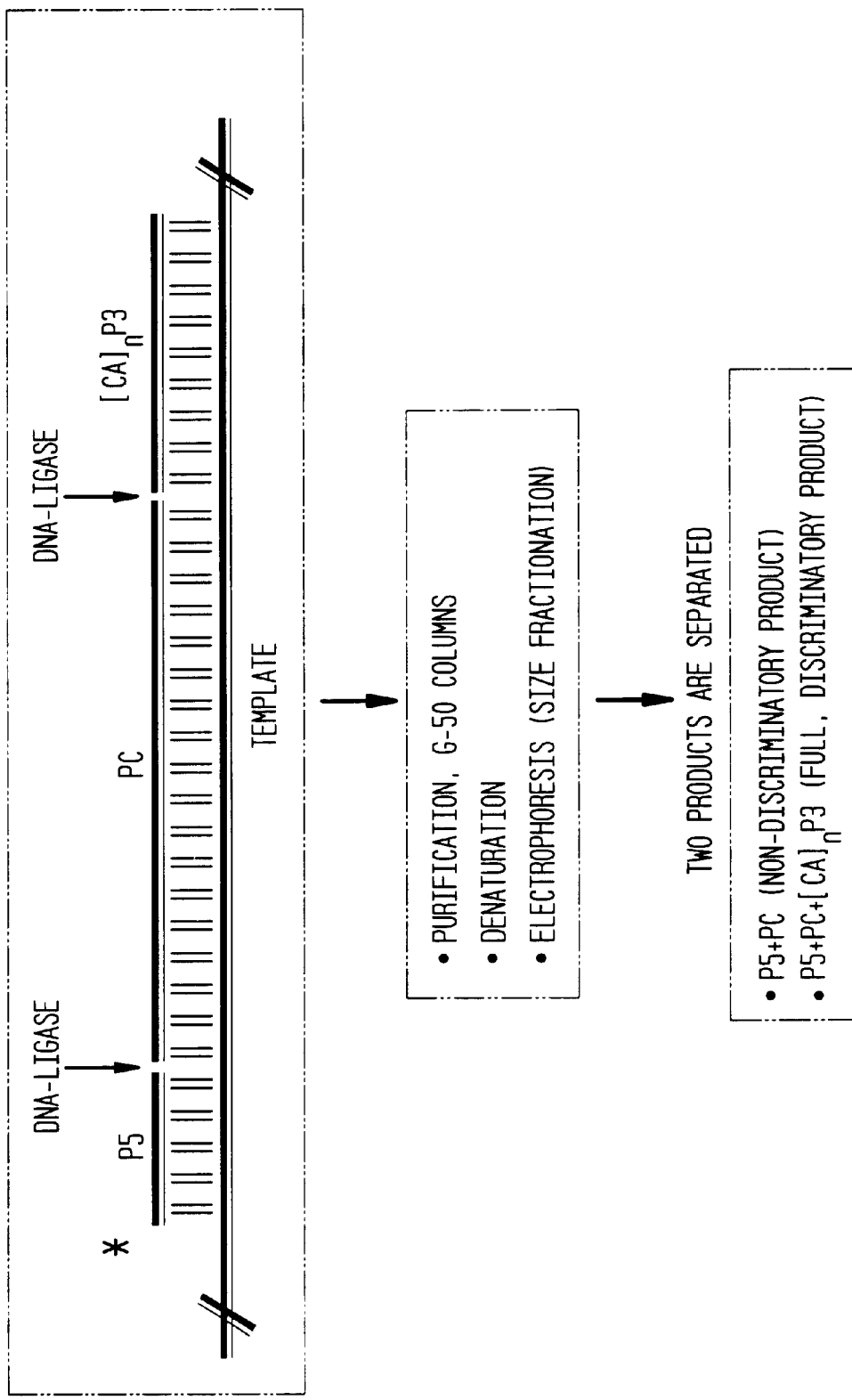

FIG. 4
GEL-FREE ANALYSIS DETECTION SYSTEM
- ATTACHMENT OF P5 TO A SOLID PHASE
- P3s ARE DIFFERENTLY LABELED
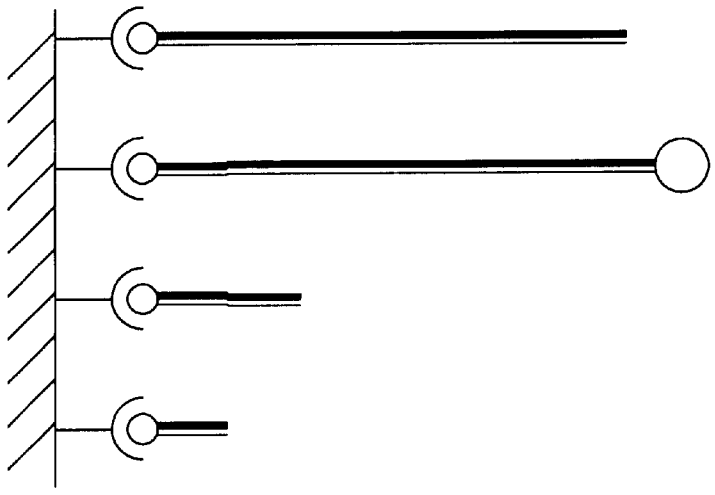
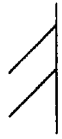 SOLID SUPPORT
 STREPTAVIDIN
 5'-BIOTINYLATED P5
———————— PC
====== P3
 [CA]P3

CASE 1: GENOTYPING A [CA]₁₃ REPEAT

FIG. 6
CASE 2: GENOTYPING A $[CA]_{14}$ REPEAT

A)

```
              L₁                    L₂
       P5 ↓        PC         ✱    ↓    P3
  ✱  NNNNNCACACA...(CA)₇...CACACA   NNNNNNNNNNNNNNNNN
     ||||||||||||||||||||||||||   |||||||||||||||||||
   ..NNNNNNNNGTGTGT...(GT)₇...GTGTGTGTNNNNNNNNNNNNNNNNNNNNNN..
                       TEMPLATE
```

ONLY $L_1$ OCCURS : NO FULL-LENGTH PRODUCT

B)

```
              L₁                    L₂
       P5 ↓        PC              ↓     [CA]ₙP3
  ✱  NNNNNCACACA...(CA)₇...CACACACANNNNNNNNNNNNNNNNNN
     |||||||||||||||||||||||||||||||||||||||||||||||
   ..NNNNNNNNGTGTGT...(GT)₇...GTGTGTGTNNNNNNNNNNNNNNNNNNNNNN..
                       TEMPLATE
```

BOTH $L_1$ AND $L_2$ OCCUR : FULL-LENGTH PRODUCT IS GENERATED

RESULTS OF GENOTYPING [CA]₁₃ AND [CA]₁₄ REPEATS

METHOD FOR GENOTYPING MICROSATELLITE DNA MARKERS

FIELD OF THE INVENTION

The present invention relates to a method for genotyping microsatellite DNA markers using ligation of at least three oligonucleotides. Specifically, the present invention provides a method for distinguishing allele content in mono-, di-, tri-, tetra-, penta-, hexa-, hepta-, octa- or nona-repeated DNA using combinations of at least three oligonucleotides comprising a 5' primer, a central primer and a plurality 3' primers that hybridize to different alleles of microsatellite DNAs.

BACKGROUND OF THE INVENTION

The analysis of variation among polymorphic DNA provides valuable tools for genetic studies in the development of genetic engineering, medicine, gene mapping and drugs. For example, variations in polymorphic DNA allows one to distinguish one individual of a population from another, or to assess the predisposition of an individual to a heritable disease or trait.

Two types of genetic markers widely used in genetic studies include microsatellites and single nucleotide polymorphisms (SNPs). Microsatellites are genomic regions that are distributed approximately every 30 kilobases throughout the genome and that contain a variable number of tandemly repeated sequences of mono-, di-, tri-, tetra-, penta-, hexa-, hepta-, octa- or nona-nucleotides. SNPs are found approximately every kilobase in the genome.

SNPs and microsatellites differ in primary DNA structure, relative genome density and genetic information. For example, SNPs are more suitable than microsatellites for genotyping with a high-density of markers because of their distribution and the high sequence specificity possessed by sequences adjacent to the SNP site. Yet, microsatellites are more informative than SNPs because microsatellites typically possess four to sixteen different alleles compared to only two alleles for SNPs.

Presently, the most commonly used methods for genotyping microsatellite markers are gel-based PCR fragment analysis (Shi et al., (1999) *Mol. Diagn.*, 4: 343–351). These methods are relatively more labor-intensive and time-consuming due to gel preparation and gel reading steps, than the method described in this invention. Moreover, the automated DNA genotyping instruments are expensive compared to other forms of detection and do not address the gel reading problems resulting from nucleotide compression. Other methods such as differential hybridization are limited by hybridization to two or more microsatellite markers that share sequences. (see Korkko et al., 1998).

Oligonucleotide Ligation Assays (OLAs) have been used to detect SNPs (Baron et al., 1996, see also U.S. Pat. Nos. 5,242,794 and 5,866,337) or mutations in a gene (Landegren et al., 1988, U.S. Pat. Nos. 4,988,617 and 6,025,139). These OLAs are designed to hybridize contiguously to single-stranded target DNA sequences. Recently, an OLA was developed to genotype microsatellites containing mono- and di-nucleotide repeats (Zirvi et al., 1999a, 1999b, U.S. Pat. No. 6,054,564, WO 98/03673, EP956359).

FIG. 1 demonstrates the methods employed in these previous OLA methods. For example, in the OLA method used for the detection of SNPs, two oligonucleotides are designed to hybridize to the region of the tested site where ligation would occur. The principle in the OLA assay for detection of mutations within a gene is to hybridize multiple short oligonucleotides contiguously throughout the entire gene. An OLA method for genotyping mono- and dinucleotide repeats has been reported where the ligation of the two oligonucleotides was performed at the middle of the repeat. In all of these methods, the presence of a mismatch would prevent hybridization and ligation of the oligonucleotide at or near the location of the mismatch.

The major drawback of using OLA for genotyping microsatellites is that ligation is not a highly discriminating process and background noise can be a significant problem. To circumvent this problem, modified nucleotides (containing nucleoside analogs) near the ligation junction are used to improve the stringency of both the hybridization and the ligation. However, this raises the cost, because relatively long, specific oligonucleotides are required for these assays. A method that overcomes these disadvantages of OLA would make this approach simpler and more efficient and amenable to the comparative genotyping of pooled DNA samples.

SUMMARY OF THE INVENTION

The present invention relates to a method for genotyping different microsatellite DNA markers using ligation of at least three oligonucleotides. In previous inventions, the principle was to hybridize combinations of two, long oligonucleotides contiguously in order to cover the whole sequence of the microsatellite. This requires the costly synthesis of specific, long oligonucleotides for each microsatellite to be genotyped. In addition, the use of modified nucleotides was necessary to achieve specificity. The present invention has eliminated these problems by using combinations of at least three oligonucleotides for each allele at a locus. Collections of limited numbers of oligonucleotides can be used for genotyping many different microsatellites, thus reducing the cost of oligonucleotide synthesis in large genotyping projects. In addition, by using combinations of three oligonucleotides, a high degree of specificity is achieved without the need to use modified nucleoside analogs.

The present invention comprises the steps of providing a sample containing microsatellite DNA; selecting combinations of at least three oligonucleotides that comprise a 5' primer, a central primer and a 3' primers; mixing the sample and primers such that the primers and microsatellite DNA hybridize; adding a ligating reagent; and detecting the presence of ligation products that consist of combinations of three oligonucleotides (5' primer, central primer and 3' primers) bound together as a single oligonucleotide with a contiguous sequence, reflecting the precise genotype of the microsatellite in the sample, and thus the allele(s) present. In particular, the 5' primer comprises at least 5 base pairs complementary to the 3' flanking region of the microsatellite target strand; the central primer is complementary to the repeated region of the microsatellite target strand DNA; and the 3' primers comprise sequences that are complementary to the 5' flanking sequence of the microsatellite target strand with the addition, at the 5' end, varying numbers of repeat units. The nature and the number of repeat units comprising the central primer depend on the nucleotides in the repeated sequence and the number of repeat units of the shortest allele at a given locus. Likewise, the number of repeat units added at the 5' end of the 3' primer also depends on the nucleotides in the repeated sequence and the number and identity (length) of the alleles in a population.

The present invention further provides a method for genotyping a DNA pool containing a mixture of different DNA samples of the same microsatellite wherein the microsatellite DNA includes mono-, di-, tri-, tetra- penta-, hexa-, hepta-, octa- or nona-nucleotide repeated alleles. The detection of the allele content of the microsatellite DNA marker within the pooled sample is determined by gel filtration, electrophoresis, mass spectrometry or a gel free analysis.

In one embodiment, the present invention provides a method for genotyping different alleles of a microsatellite DNA wherein the 5' end of the 5' primer is labeled with a detectable label. In another embodiment, the method provides detection of different allele of a microsatellite DNA wherein the 5' or 3' primer is covalently linked to a functional group, wherein the functional group is capable of specifically binding to a component of a solid support.

The present invention will decrease cost and improve the experimental quality needed to achieve genotyping using high density DNA pooling. The method uses the capacity of DNA ligase to join selectively designed adjacent oligonucleotides that hybridize to a given DNA template. The combination of specifically designed oligonucleotides for each allele within a marker will allow discrimination between the different genotypes.

DESCRIPTION OF THE FIGURES

FIG. 1 shows other prior techniques for OLA. In particular, the top figure demonstrates an assay for the detection of mutations within a gene. (Landergren et al. 1988; U.S. Pat. Nos. 4,988,617 and 6,025,319). The middle figure demonstrates an OLA for the detection of SNPs. (Baron et al.; U.S. Pat. Nos. 5,242794 and 5,866,337). The bottom figure demonstrates an OLA for genotyping mono- and dinucleotide repeats. (Zirvi et al., 1999a, 1999b, U.S. Pat. No. 6,054,564). The template is a single-stranded DNA containing the complementary sequence which the oligonucleotides are hybridizing. The letter "L" points the ligation sites.

FIG. 2: Oligonucleotide Ligation Assay Principle

FIG. 2 describes the components of the oligonucleotides of the present invention and demonstrates the ligation method.

FIG. 3: Protocol of Present Invention

FIG. 3 shows an embodiment of the method of the present invention diagrammatically.

FIG. 4: Design of a Gel Free Assay

FIG. 4 shows a second embodiment of the present invention as a gel free detection assay. In this scheme, the different oligonucleotide combinations will give different signals thus indicating the allele content of the sample. P5 and ligated P5-PC will not provide any signal.

FIGS. 5A & B shows an example of the present invention for genotyping a $[CA]_{13}$ Repeat DNA.

FIGS. 6A & B: Case 2: Genotyping a $[CA]_{14}$ Repeat

FIGS. 6A & B shows an example of the present invention for genotyping a $[CA]_{14}$ repeat DNA.

Figure 1:
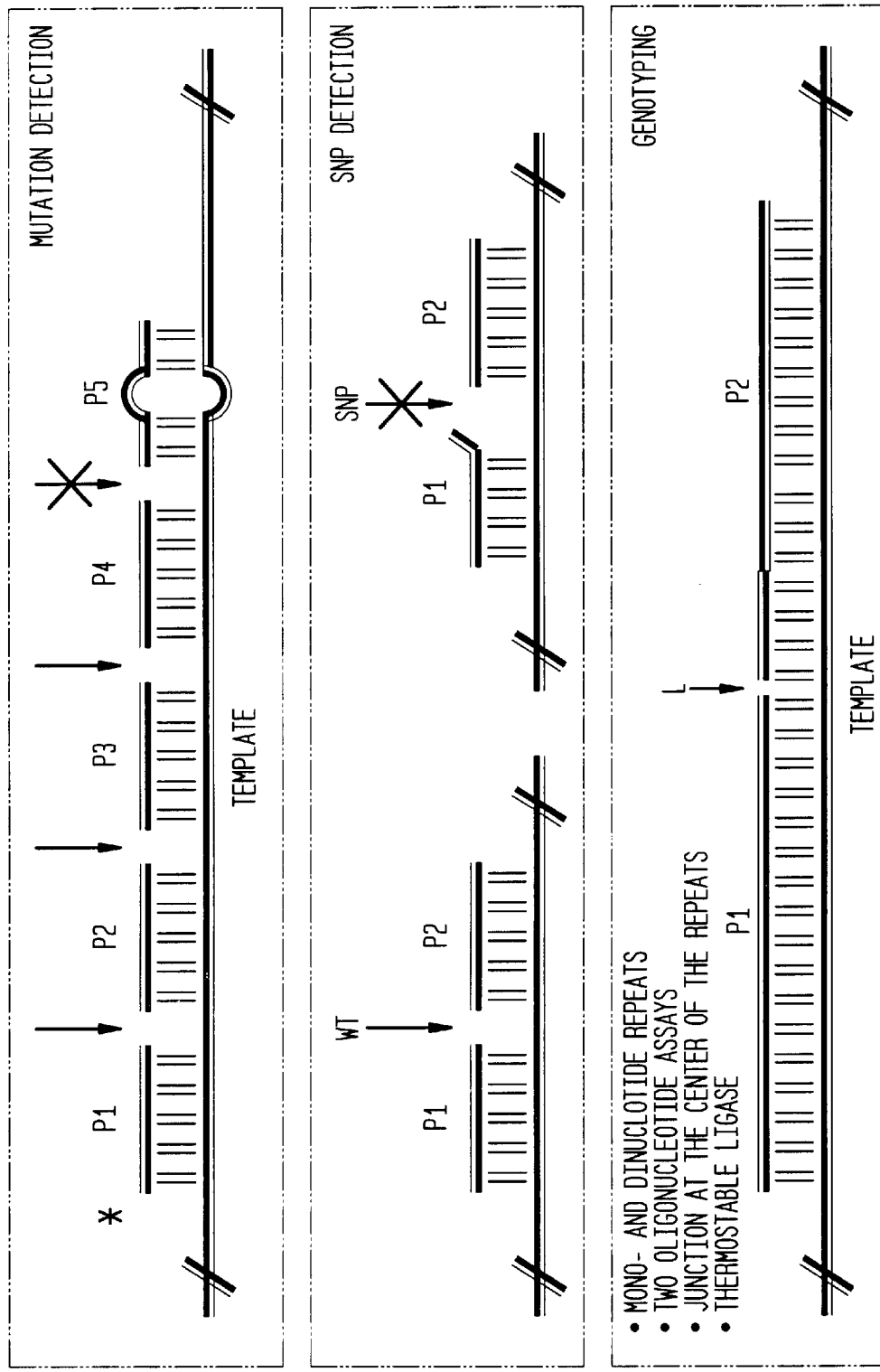
FIG. 1: Prior Art Oligonucleotide Ligation Assay (OLA) Techniques

The top figure demonstrates the use of the present invention in genotyping CA- repeated microsatellite; a $[CA]_{13}$ homozygous (left); a $[CA]_{14}$ homozygous (middle) and a $[CA]_{13-14}$ heterozygous, (right), respectively. The bottom figure shows three control lanes to demonstrate the specificity of the generated ligation products: the reaction mixture contains all reagents except the P3 oligonucleotide (left lane), no ligase (middle lane) and no DNA template (right lane).

DEFINITIONS

Throughout the description of the present invention, several terms are used that are specific to the technology of this field. For the sake of clarity and to avoid any misunderstandings, these definitions are provided:

Allele: At a given locus, a particular form of a gene or genotype, specifying one of all the possible forms of the character encoded by this locus. A diploid genome contains two alleles at any given locus.

Discriminating Primers: A set of primers that are individually specific for one allele, depending on the number of repeat units that the primers possess at either their 3' or 5' end. These primers differentiate between the different alleles.

Functional group: A moiety of chemical or proteinaeous nature that is attached to either the 5' end or the 3' end of an oligonucleotide allowing the latter to be purified by affinity.

Genotype: Set of alleles at a specified locus.

Hybridization: The process by which two nucleic acids are linked together by base pairing, forming a duplex DNA of complementary sequences. In this description, the hybridization occurs between oligonucleotides and the PCR-amplified template. The conditions of the assay are designed to reach a perfectly matched duplex between the oligonucleotides and the template.

Label: An attachment linked to an oligonucleotide that permits its specific detection via the signal emitted by the attachment.

Ligase: An enzyme that catalyzes the formation of a phosphodiester bond at the site of single-stranded break within a DNA duplex.

Ligation: The process catalyzed by a DNA ligase.

Locus: A specified region of the genome.

Microsatellite: DNA of eukaryotic cells comprising highly repetitive DNA sequences flanked by sequences unique to that locus. In this description, microsatellite refers to mono-, di-, tri-, tetra penta-, hexa-, hepta-, octa-, or nona-nucleotide repeated regions.

Oligonucleotide: A short single-stranded deoxyribonucleic acid molecule. In this description, the. length of the oligonucleotides varies from 5 bases to more than 32 bases.

Polymerase Chain Reaction (PCR) amplification: An enzymatic process resulting in the exponential amplification of specific region of a DNA template. The process uses a thermostable polymerase, capable of replicating a DNA template from a primer. In the presence of two primers, the region between them is amplified following this process.

Thermostable ligase: A heat resistant enzyme capable of performing ligase functions.

DETAILED DESCRIPTION OF THE INVENTION

Figure 5:
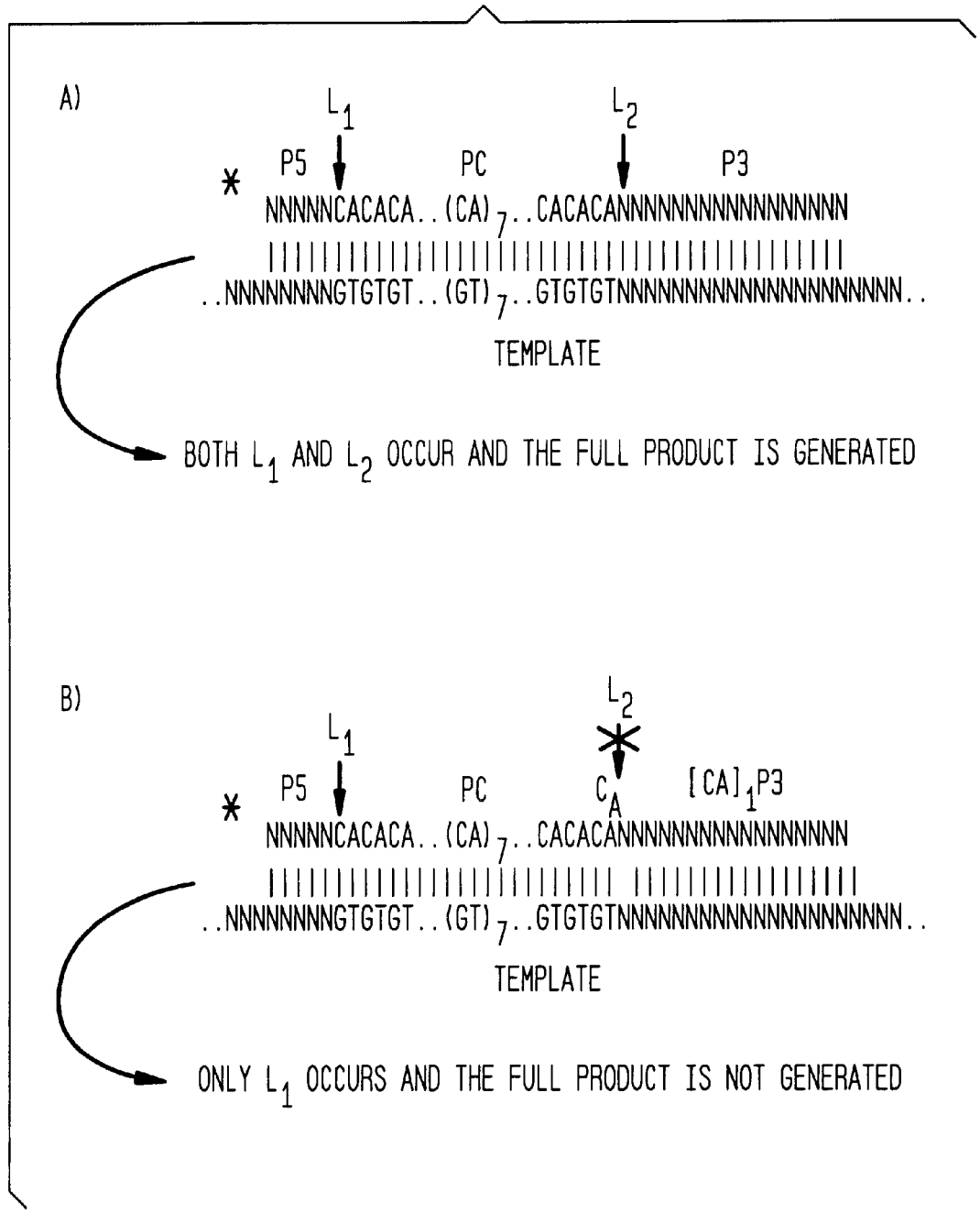
FIGS. 5A & B: Case 1: Genotyping a $[CA]_{13}$ Repeat
Figure 7:
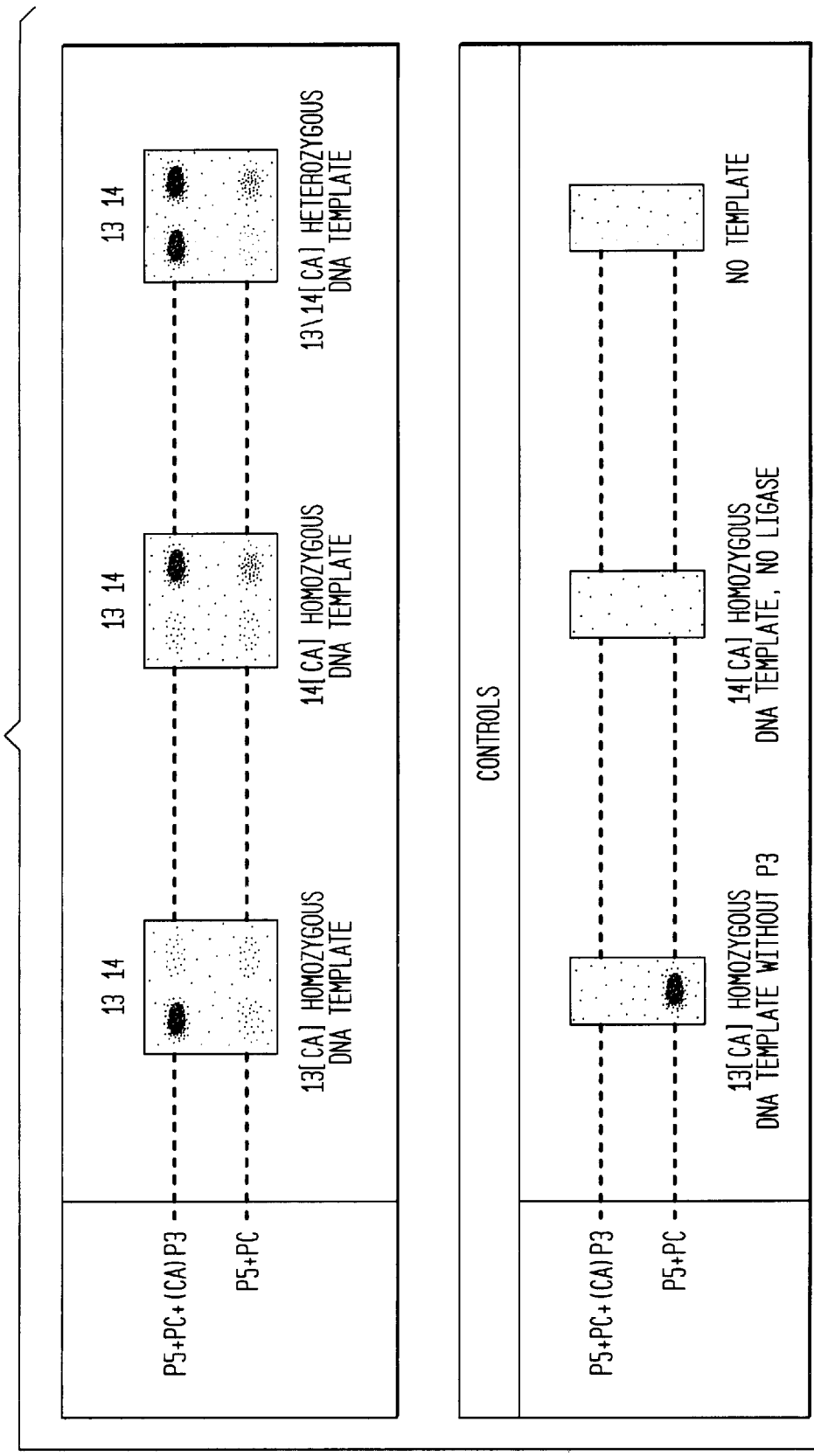
FIG. 7: Results of Genotyping $[CA]_{13}$ and $[CA]_{14}$ Repeats

The present invention relates to a method for genotyping different alleles of microsatellite DNA by using a combination of at least three oligonucleotides for each allele on the locus. In particular, the present method comprises providing a sample containing the microsatellite DNA; selecting combinations of at least three oligonucleotides comprising a 5' primer (P5), wherein the 5' primer comprises at least 5 base pairs complementary to the 3' flanking region of the repeated region of the microsatellite DNA; a central primer (PC), wherein the central primer is complementary to the repeated region of the microsatellite DNA; and at plurality of 3' primers ([repeat-unit]$_n$P3), which comprises a sequence that is complementary to the 5' flanking sequence of the repeat region of the microsatellite, and which possesses at its 5' end, a number (n=0, 1, 2 . . . ) of repeat units of the microsatellite to genotype, in particular, cytosine-adenine, (hereinafter, "[CA]$_n$") for a CA repeated DNA, mixing the sample and primers such that the primers and microsatellite DNA hybridize; adding a ligating reagent; and detecting the presence of full ligation products that consist of the three oligonucleotide primers linked together in a contiguous sequence. (see FIGS. 3–7).

The principle described in the present invention holds for any changes in the orientation, length and modifications of the oligonucleondes. One skilled in the art could easily design a scheme in which the discriminating primers were the 5' primers, P5[repeat-unit]$_n$. In particular, the present invention further provides a plurality of 5' primers ([repeat-unit]$_n$P5) which comprise a sequence that is complementary to the 3' flanking sequence of the repeat region of the microsatellite, and which possesses at its 3' end, a number (n=0, 1, 2 . . . ) of repent units of the microsatellite to genotype, in particular, cytosine-adenine, (hereinafter, "[CA]$_n$") for a CA repeated DNA; a central primer, PC, wherein the central primer is complementary to the repeated region of the target strand of the microsatellite DNA and and a 3' primer P3, of a fixed length, wherein P3 comprises at least 5 base pairs that are complementary to the 5' flanking region of the repeated region of the target microsatellite DNA strand.

The design of the oligonucleotides for the present invention provides a low cost technology. In particular, the present invention provides oligonucleotides wherein the 5' primer, P5, is at least a 5-mer wherein a collection of 1024 oligonucleotides ($N^5$=A, C, G, or T) cover all possible sequences of this size. The 3' primer can be a 5-mer or greater, preferably a 10 to 17-mer (excluding the repeat units at its 5' end). The central primer or repeat oligonucleotides can be used for the genotyping of many microsatellites of the same repeat type, and a relatively small collection of approximately 500 different oligonucleotides are sufficient for genotyping of the vast majority of microsatellite loci.

The present invention will not only increase the throughput of the process at low cost, but it will also increase the precision and accuracy of genotyping, that is expected to allow cost-effective genotyping of pooled DNA samples. The present method uses the capacity of the DNA ligase to join selectively designed adjacent oligonucleotides that hybridize to a given DNA template. (see FIG. 3). Combination of specifically designed oligonucleotides for each allele in the marker in the assay will allows determination of the allele content within the DNA sample.

Therefore, in one embodiment of the present invention, the ligation reagent is T4 DNA ligase or a thermostable ligase. However, one skilled in the art could use any ligase known in the field to facilitate the ligation step.

The present invention uses combinations of three oligonucleotides, P5, PC and P3, wherein the 5' primer, P5, hybridizes to the complementary 3' flanking region of the microsatellite, the central primer, PC, hybridizes to the complementary repeated region of the microsatellite and the 3' primers, [repeat-unit]$_n$P3, hybridize to the 5' complementary flanking region of the microsatellite. (see FIG. 2).

In a preferred embodiment, P5 comprises a 5-mer sequence complementary to the flanking region of the repeat and is radio labeled at its 5'-end. Therefore, in one embodiment, the detecting step further comprises labeling the 5' end of the 5' primer with a detectable label. PC comprises the complementary sequence of the repeat and its length is dictated by the shortest allele found at that particular microsatellite marker in the population. The [repeat-unit]$_n$P3 is an ensemble of primers with a core sequence complementary to the 5' flanking sequence of the target strand and with a varying number (n=0, 1, 2, 3, . . . ) of repeat units at its 5' end. The number of repeat added at the 5' end of [repeat-unit]$_n$P3 is for the genotyping of all the existing alleles of the microsatellite marker.

The use of the present invention to perform genotyping with pooled DNA will increase the value of the results of the assay. Therefore, in one embodiment of the present invention, the sample is a mixture of different samples containing a given microsatellite locus from a number of individuals.

By way of example, the present invention demonstrates the genotyping of the D6S471 locus which is a dinucleotide [CA]-repeat microsatellite marker harbouring four different alleles, $[CA]_{13}$, $[CA]_{14}$, $[CA]_{16}$ and $[CA]_{17}$. Dinucleotide markers represent a degree of complexity, intrinsic to their primary structure, suitable for the experimental development needed to achieve both specificity and stability of DNA hybridization. The methodology developed in genotyping this locus is applicable to genotyping mono-, di-, tri-, tetra-, penta, hexa-, hepta-, octa- and nona-nucleotide microsatellites. Therefore, in another embodiment, the present invention, provides a method for genotyping different microsatellite DNA at a locus by using a combination of at least three oligonucleotides for each allele on the loci wherein the sample of microsatellite DNA consist of mono-, di-, tri-, tetra-, penta, hexa-, hepta-, octa- and nona-repeated alleles.

In yet another embodiment, the sample is an amplified PCR fragment of the microsatellite DNA.

Other systems use only two oligonucleotides with one ligation event which implies that for each microsatellite, there is a need to synthesize long, specific oligonucleotide. In addition, modified nucleosides are often used to improve stringency of the hybridization step. These conditions increase the cost of large scale genotyping projects. The present invention uses combinations of three oligonucleotides, P5, PC and [repeat-unit]$_n$ P3 and two ligation to link the three oligonucleotides together which improves the specificity and eliminates the need for long oligonucleotides. In addition, specificity is achieved without using modified nucleosides.

Following hybridization of the three oligonucleotides onto the template, the DNA ligase joins them. After passing the ligation products through a G-50 column, they are separated by gel electrophoresis. Since P5 is radiolabelled at its 5' end (*), only two ligation products will be visible upon exposure on a X-ray film, P5-PC and P5-PC-P3. While the former is genotype-independent, the latter will be formed exclusively when the particular combination of oligonucleotides hybridize perfectly to a given template, thus reflecting the genotype or allele content of the locus. Therefore, in one embodiment of the present invention, the detecting step comprises separating the ligation products according to their size by gel electrophoresis.

However, a gel-free analysis system would provide automation and efficiency. In another embodiment, the present invention provides a method for detecting the ligation products by a gel free system wherein the gel free system comprises covalently linking a functional group to the 5' end of the 5'-primer, P5, wherein the functional group exhibits specific binding to a component of a solid support; and labeling the 3' end of the 3'-primers, [repeat-unit]$_n$P3, with different detectable labels wherein the different labels yield different signals. (see FIG. 4). The different 3'-labels for each 3'-primer will differentiate and/or discriminate between genotypes by revealing a different signal (or signals) depending upon which oligonucleotide combination(s) will ligate together. In one embodiment, the detectable labels are fluorescent labels. In still another embodiment, the functional group is biotin and the solid support is coated with streptavidin.

In another embodiment, the present invention provides a method for detecting the ligation products by a gel free system wherein the gel free system comprises covalently linking a functional group to the 3' end of the 3'-primer, P3, wherein the functional group exhibits specific binding to a component of a solid support; and labeling the 5' end of the 5'-primers, [repeat-unit]$_n$P5 with different detectable labels wherein the different labels yield different signals. The different 5'-labels for each 5'-primer will differentiate and/or discriminate between genotypes by revealing a different signal (or signals) depending upon which oligonucleotide combination(s) will ligate together. Therefore, the different labels attached to the discriminating primers would be attached to the 5' end of P5[repeat-unit]$_n$. In one embodiment, the detectable labels are fluorescent labels. In still another embodiment, the functional group is biotin and the solid support is coated with streptavidin.

The present invention further provides a kit for detection of the presence of different alleles at a locus by using a combination of at least three oligonucleotides wherein the oligonucleotides comprise sequences which are complementary to and hybridize with one strand of the repeat region of a microsatellite DNA and having terminal groups such that the oligonucleotides are ligatable to each other when hybridized perfectly to the microsatellite DNA.

In one embodiment of the present invention, a kit for the detection of the presence of different microsatellite DNA at a locus comprises combinations of at least three oligonucleotides and instructions for use of the oligonucleotides in a suitable container means, wherein the oligonucleotides comprise sequences which are complementary to and hybridize with one strand of the repeat region of a microsatellite DNA, wherein the oligonucleotides comprise terminal groups such that the oligonucleotides are ligatable to each other when hybridized to the microsatellite DNA. In another embodiment, the kit comprises a 5' primer; a central primer; a plurality of 3' primers, and a ligating reagent. In another embodiment, at least of one of the oligonucleotides is labeled with a detectable label. In a preferred embodiment, the label is a fluorescent label.

In yet another embodiment, the present invention provides a kit for detection of the presence of different alleles at a locus by separating the ligation products by a gel free system wherein the kit comprises combinations of at least three oligonucleotides and instructions for use of the oligonucleotides in a suitable container means, wherein the oligonucleotides comprise at least one primer that is covalently-linked to a functional group, wherein the functional group exhibits specific binding to a component of a solid support and at least one other primer is labeled with different detectable labels, wherein the different labels yield different signals.

In another embodiment, the kit comprises a 5' primer that is covalently linked to a functional group at its 5' end of the 5' primer; a central primer; a plurality of 3' primers that are labeled at their 3' end with different detectable labels wherein the different labels yield different signals (discriminating P3-primers); a ligating reagent, and a solid support. In a preferred embodiment, the detectable labels are different fluorescent labels. Still further, in another embodiment of the present kit, the functional group is biotin and the solid support is coated with streptavidin.

In another embodiment, the kit comprises a 3' primer that is covalently linked to a functional group at its 3' end of the 3' primer; a central primer; a plurality of 5' primers that are labeled at their 5' end with different detectable labels wherein the different labels yield different signals (discriminating P5-primers); a ligating reagent, and a solid support. In a preferred embodiment, the detectable labels are different fluorescent labels. Still further, in another embodiment of the present kit, the functional group is biotin and the solid support is coated with streptavidin.

EXAMPLES

These examples demonstrate the genotyping of homozygous and heterozygous templates of 13 and 14 [CA] repeats. The oligonucleotides were phosphorylated where the 5' primer, P5, was radiolabeled. The target template was an enriched single stranded DNA resulting from an asymmetric PCR reaction of the microsatellite to genotype and was purified on a Sephadex column (G-50 micro spin, Pharmacia). The DNA template and the oligonucleotides were first heat-denatured (by transferring the respective tubes in boiling water for three minute)s. The following components were mixed at room temperature: five picomoles of each of the oligonucleotides, 3 microliters of formamide (final concentration of 30%), 2 microliters of 5× ligase buffer (Gibco/BRL) and 0.4 micrograms of SSBP (Single Stranded Binding Protein, Promega). Then, 0.5 picomoles of the template was added to the mixture and 1 microliters of ligase (8 units, Gibco/BRL) was added immediately after. After an incubation of 5 minutes at room temperature, the reaction was stopped by heating (three minutes at 95° C.). The ligation products were then separated by gel electrophoresis in a 12% denaturing polyacrylamide gel. Using these conditions, templates of [CA]$_{13}$ versus [CA]$_{14}$ and vice versa, as well as heterozygous templates of 13 and 14 CA (see FIG. 7) were specifically genotyped. No modified nucleosides were used in these assays.

When P5, PC and P3 (without any [CA]$_0$ unit at its 5' end) were hybridized onto a [CA]$_{13}$ template, there were no gaps or bulges due to unpairing bases and both junctions (P5-PC and PC-P3) are ligated. The full discriminatory product was generated. In contrast, when P5, PC and [CA]$_1$P3 are hybridized on a [CA]$_{13}$ template, the [CA] unit of [CA]$_1$P3 bulged out, thus preventing ligation. Note that the bulged [CA] was also found at the P5-PC junction, but the ligated PC-[CA]$_1$P3 was not visible upon exposure on an X-ray film.

Example I Genotyping [CA]$_{13}$

For example, when genotyping. a template of [CA]$_{13}$, only the combination P5-PC-[CA]$_0$P3 ligate (see FIG. 5A) The combination P5-PC-[CA]$_1$P3 did not ligate on this teraplate because a [CA] unit bulged out at the junction of either P5-PC or PC-[CA]$_1$P3 thus preventing ligation event to occur (see FIG. 5B)

Example II Genotyping [CA]$_{14}$

When genotyping a template of [CA]$_{14}$, the ligated combination was P5-PC-[CA]$_1$P3 see FIG. 6A ). The combination P5-PC-P3 did not ligate an a template of [CA]$_{14}$ because a gap of dinucleotide [CA] existed between P5 and PC or between PC and P3 (see FIG. 6B).

When P5-PC and [CA]$_0$P3 are hybridized onto a [CA]$_{14}$ template, there was a gap of one [CA] unit at either the P5-PC or PC-[CA]$_0$P3 junction and the full, discriminatory product was not generated. However, P5, PC and [CA]$_1$P3 hybridize perfectly on the [CA]$_{14}$template and the full product was generated.

Example III Genotyping the D6S471 locus

The genotype of the D6S471 locus was determined as an example of the present invention. This locus was a dinucleotide [CA]-repeat microsatellite marker harbouring four different alleles, [CA]$_{13}$, [CA]$_{14}$, [CA]$_{16}$ and [CA]$_{17}$. Dinucleotide markers represent a degree of complexity, intrinsic to their primary structure, suitable for the experimental tuning needed to achieve both specificity and stability of DNA hybridization. The methodology developed in genotyping this locus is thus applicable to mono-, di-, tri-, tetra, penta-, hexa-, hepta-, octa- and nona-nucleotide microsatellites.

In the case of D6S471, PC consists of [CA]$_{13}$. The various P3 oligonucleotides were of different lengths and consist of a core sequence complementary to the 5'-repeat-adjacent sequence, and of a number of n of [CA] units at its 5' end (where n represents all number of dinucleotide necessary to fill the sequence gap to PC, reflecting thus all alleles in the population at that locus).

In the present model case, there were four different P3 reflecting the four alleles at the D6S471 locus. For example, when genotyping a template of [CA]$_{13}$, only the combination P5-PC-P3 ligated (see FIG. 5A). The combination P5-PC-[CA]$_1$P3 did not ligate on this template because a [CA] unit bulged out at the junction of either P5-PC or PC-[CA]$_1$P3 (se FIG. 5B). When genotyping a template of [CA]$_{14}$, The ligated combination was P5-PC-[CA]$_1$ P3 (see FIG. 6A.) The combination P5-PC-P3 did not ligate on a template of [CA]$_{14}$ because a gap of diniucleotide [CA] existed between P5 and PC or between PC and [CA]$_0$P3 (see FIG. 6B).

This application incorporates by reference the following publications:

References

1. Barany, F. (1991) *Proc. Natl. Acad. Sci. USA*, 88: 189–193.
2. Baron, H., Fung, S., Aydin, A., Bahring, S., Luft, F. C. & Schuster H. (1996) *Nat. Biotechnol.*, 14: 1279–1282.
3. Hahner, S., Schneider, A., Ingendoh, A. & Mosner, J. (2000) *Nucleic Acids Res.* 28:382.
4. Harada, K. & Orgel, L. E. (1993) *Nucleic Acids Res.*, 21: 2287–2291.
5. Housby, J. N. & Southern, E. M. (1998) *Nucleic Acids Res.*, 26: 4259–4266
6. Housby, J. N., Thorbjarnardottir, S. H., Jonsson, Z. O. & Southern, E. M. (2000) *Nucleic Acids Res.*, 28: e10.
7. Jackson, P. E., Scholl, P. F. & Groopman, J. D. (2000) *Mol. Med. Today*, 6:271–276.
8. Korkko, J., Annunen, S., Pihlajamaa, T., Prockop, D. J. & Ala-Kokko, L. (1998) *Proc. Natl. Acad. Sci. USA*, 95: 1681–1685.
9. Landegren, U., Kaiser, R., Sanders, J. & Hood, L. (1988) *Science*, 241: 1077–1080.
10. Pritchard, C. E. & Southern, E. M. (1997) *Nucleic Acids Res.*, 25: 3403–3407.
11. Shi, M. M., Bleavins, M. M. & de la Iglesia, F. A. (1999) *Mol. Diagn.*, 4: 343–351.
12. Wada, Y., Mitsumori, K., Terachi, T. & Ogawa, O. (1999) *J. mass Spectrom.*, 34:885–888.
13. Wu, D. Y. & Wallace, R. B. (1989) *Gene*, 76: 245–254.
14. Zirvi, M., Bergstrom, D. E., Saurage, A. S., Hammer, R. P. & Barany, F. (1999a) *Nucleic Acids Res.*, 27: e40.
15. Zirvi, M., Nakayama, T., Newman, G., McCaffrey, T., Paty, P. & Barany, F. (1999b) *Nucleic Acids Res.*, 27: e41.

U.S. Pat. No. : 4,988,617 Jan., 1991 Landegren, et al.
U.S. Pat. No. : 5,242,794 Sep., 1993 Whiteley, et al.
U.S. Pat. No. : 5,800,994 Sep., 1998 Martinelli et al.
U.S. Pat. No. : 5,866,337 Feb., 1998 Schon
U.S. Pat. No. : 6,025,139 Feb., 2000 Yager, et al.
U.S. Pat. No. : 6,054,564 Apr., 2000 Barany, et al.
WO 91/17239
WO 95/27078
WO 98/03673
EP 956359

What is claimed is:

1. A method for genotyping different alleles of a microsatellite DNA locus said microsatellite DNA locus having a repeat region and further having a predetermined number of different alleles, each allele having a different number of microsatellite repeat units in said repeat region, said method comprising:

(a) providing a sample containing the microsatellite DNA locus;

(b) providing a set of oligonucleotides comprising:
 (i) a 5' primer complementary to a 3' flanking region of the repeat region of the microsatellite DNA locus;
 (ii) a central primer comprising a number of primer repeat units complementary to the repeat region corresponding to the allele having the least number of said microsatellite repeat units; and,
 (iii) an ensemble of discriminating 3' primers comprising a plurality of 3' primers each of which has the formula of $XY_n$, wherein
  X is a sequence that is complementary to the a 5' flanking sequence of the repeat region of the microsatellite DNA
  Y is a primer repeat unit located at the 5' end of each of said 3' primers which contains said primer repeat unit, the primer repect unit complementary to the microsatellite repeat unit; and,
  n is the number of primer repeat units in any one of said discriminating 3' primers
  wherein n is a varying number selected such that a combination of oligonucleotides comprising said 5' primer, said central primer and any one of said discriminating 3' primers is complementary to one of said predetermined number of different alleles of the DNA microsatellite locus;

(c) mixing the sample and primer such that the primers and microsatellite DNA hybridize;

(d) adding a ligating reagent;

(e) detecting the presence of a ligation product that incorporates three oligonucleotides, said three oligonucleotides comprising said 5' primer, said central primer and one of said discriminating 3' primers; and (f) deducing the genotype of the sample according to the identities of the oligonucleotides incorporated in a ligation product.

2. The method according to claim 1, wherein the sample is a mixture of different samples containing different alleles of a given microsatellite DNA locus.

3. The method according to claim 1, wherein the microsatellite DNA locus comprises mono-, di-, tri-, tetra-, penta-, hexa-, hepta-, octa- and nona-nucleotide repeated alleles.

4. The method according to claim 1, wherein the sample is an amplified PCR fragment of the microsatellite DNA locus.

5. The method according to claim 1, wherein the oligonucleotides comprise of modified nucleosides.

6. The method according to claim 1, wherein the selecting step further comprises labeling the 5' end of the 5' primer with a detectable label.

7. The method according to claim 1, wherein the detecting step comprises separating the ligation products according to their size by gel electrophoresis.

8. The method according to claim 1, wherein the ligation reagent is T4 DNA ligase or a thermostable ligase.

9. The method according to claim 1, wherein the detecting step further comprises separating the ligation products by a gel free system wherein the gel free system comprises covalently linking a functional group to the 5' end of the 5' primer wherein the functional group exhibits specific binding to a component of a solid support; and labeling the 3' end of the 3' primers with different detectable labels wherein the different labels yield different signals.

10. The method according to claim 9, wherein the detectable labels are fluorescent labels.

11. The method according to claim 9, wherein the functional group is biotin and the solid support is coated with streptavidin.

12. The method according to claim 1 wherein said 5' primer is a single primer comprising a 5 base sequence and said central primer is a single primer.

13. The method according to claim 1 wherein the total number of discriminating 3' primers is equal to the number of different alleles.

14. A method for genotyping, different alleles of a microsatellite DNA locus, the locus comprising a repeat region with a flanking region located at each end of the repeat region, the microsatellite DNA locus having a repeat region and further having a predetermined number of different alleles, each allele having a different number of microsatellite repeat units in said repeat region, said method comprising:

(a) providing a sample confining the microsatellite DNA locus;

(b) providing a set of oligonucleotides comprising:
  (i) a single primer complementary to a flanking region located at one end of the repeat region of the microsatellite DNA locus;
  (ii) a central primer complementary to the repeat region corresponding to the allele having the least number of sad microsatellite repeat units; and,
  (iii) an ensemble of discriminating primers comprising a plurality of primers, each of which has the formula of $XY_n$, wherein X is a sequence that is complements to the flanking region located at the opposite end of the repeat region recited in step (b)(i);

Y is a primer repeat unit complementary to the microsatellite repeat unit; and n is the number of primer repeat units in any one of said discriminating primers, wherein n is a varying number selected such that a combination of oligonucleotides comprising said single primer, said central primer and any one of said discriminating primers is complementary to one of said predetermined number of different alleles;

(c) mixing the sample and primers such that the primers and microsatellite DNA hybridize;

(d) adding a ligating reagent; and (e) detecting the presence of a ligation product that incorporates three oligonucleotides, said three oligonucleotides comprising said single primer, said central primer and one of said discriminating primers;

(f) deducing the genotype of the sample according to the identities of the oligonucleotides incorporated in a ligation product.

15. The method according to claim 14 wherein said single primer is a single primer comprising a 5 base sequence and said central primer is a single primer.

16. The method according to claim 14 wherein the plurality of discriminating primers is equal in number to the number of different alleles at the locus.

17. The method according to claim 14 wherein the sample is a mixture of different samples containing different alleles of a given microsatellite DNA.

18. The method according to clam 14 wherein the microsatellite DNA locus comprises of mono-, di-, ti-, tetra-, penta-, hexa-, octa- and nona nucleotide repeat alleles.

19. The method according to claim 14 wherein the sample is an amplified DNA fragment of the microsatellite DNA locus.

20. The method according to claim 14 wherein the oligonucleotides comprise of modified nucleosides.

21. The method according to claim 14 wherein the step of providing a set of oligonucleotides further comprises labelling an end of the single primer.

22. The method according to claim 14 wherein the detecting step comprises separating the ligation product according to their size by gel electrophoresis.

23. The method according to claim 14 wherein the ligation reagent is T4 DNA ligase or a thermostable ligase.

24. The method according to claim 14 wherein the detecting step further comprises separating the ligation product by a gel tree system wherein the gel free system comprises covalently linking a functional group to the end of the single primer wherein the functional group exhibits specific binding to a component of a solid support; and labelling an end of X with different detectable labels wherein the different labels yield different signals.

25. The method according to claim 24 wherein the detectable labels are fluorescent labels.

26. The method according to claim 24 wherein the functional group is biotin and the solid support is coated with streptavidin.

* * * * *